(12) United States Patent
Halberthal et al.

(10) Patent No.: US 8,193,938 B2
(45) Date of Patent: Jun. 5, 2012

(54) APPARATUS FOR IDENTIFYING AND TRACKING MULTIPLE TOOLS AND DISPOSABLES

(75) Inventors: Reuven Halberthal, Tel Aviv (IL); Jacob Poremba, Nes Ziona (IL)

(73) Assignee: Haldor Advanced Technologies Ltd. (IL)

( * ) Notice: Subject to any disclaimer, the term of this patent is extended or adjusted under 35 U.S.C. 154(b) by 522 days.

(21) Appl. No.: 12/369,762

(22) Filed: Feb. 12, 2009

(65) Prior Publication Data

US 2010/0201487 A1    Aug. 12, 2010

(51) Int. Cl.
G08B 13/14    (2006.01)
(52) U.S. Cl. .................. 340/572.7; 340/572.8; 343/742
(58) Field of Classification Search ............... 340/572.1, 340/572.7, 572.8, 10.1; 343/741, 742
See application file for complete search history.

(56) References Cited

U.S. PATENT DOCUMENTS

| | | | |
|---|---|---|---|
| 5,650,596 A | 7/1997 | Morris | |
| 5,923,001 A | 7/1999 | Morris | |
| 6,366,206 B1 * | 4/2002 | Ishikawa et al. | 340/572.1 |
| 6,703,935 B1 | 3/2004 | Chung | |
| 6,777,623 B2 | 8/2004 | Ballard | |
| 6,998,541 B2 | 2/2006 | Morris et al. | |
| 7,411,506 B2 * | 8/2008 | Volpi et al. | 340/572.4 |
| 2001/0000659 A1 | 5/2001 | Hayashi | |
| 2003/0052788 A1 * | 3/2003 | Chung | 340/572.8 |
| 2006/0043179 A1 * | 3/2006 | Nycz et al. | 235/385 |
| 2006/0044137 A1 | 3/2006 | Morris et al. | |
| 2006/0187059 A1 * | 8/2006 | Fabian et al. | 340/572.8 |
| 2006/0232407 A1 * | 10/2006 | Ballard | 340/572.1 |
| 2007/0125392 A1 | 6/2007 | Olson, Jr. et al. | |
| 2007/0247318 A1 * | 10/2007 | Pempsell et al. | 340/572.8 |
| 2007/0257857 A1 | 11/2007 | Marino | |
| 2008/0001760 A1 * | 1/2008 | Oh et al. | 340/572.7 |
| 2008/0129629 A1 * | 6/2008 | Kimura et al. | 343/788 |
| 2008/0174409 A1 * | 7/2008 | Frank | 340/10.4 |
| 2008/0272913 A1 * | 11/2008 | Barnes et al. | 340/572.1 |
| 2010/0179822 A1 * | 7/2010 | Reppas | 340/10.1 |

FOREIGN PATENT DOCUMENTS

WO    WO/96/04530    2/1996
WO    WO/2010/092570    8/2010

* cited by examiner

Primary Examiner — Thomas Mullen (57) ABSTRACT

A method and apparatus for identifying and tracking instruments, in multiple instrument environments such as an operating room or a garage. Each instrument or disposable has attached thereto an identifying tag, such as an RFID tag. Each plane or location the instruments or disposables are placed on, comprises an antenna and thus continuously identifies the tools. In order for the antenna to work in a metallic environment, the antenna is equipped with a metallic board underneath, which insulates form other metals, and in order for the metallic board not to absorb all the energy, a spacing layer is placed between the metal board and the antenna. Flat antennas may be implemented as a collection of wire loops, overlapping in about 20% of one of their dimensions.

15 Claims, 8 Drawing Sheets

APPARATUS FOR IDENTIFYING AND TRACKING MULTIPLE TOOLS AND DISPOSABLES

TECHNICAL FIELD

The present invention relates in general to complex environments in which tools or disposables are used, and in particular to a device for identifying and tracking tools and disposables.

BACKGROUND

There are many environments in which multiple tools and disposables are used, including for example operation rooms, hangars, garages, or the like.

An operation room is a facility in which intrusive operations are performed on patients. Typically, multiple people participate in an operation, including a chief surgeon, sometimes an assistant surgeon, an anesthesiologist, a scrub nurse, and a circulating nurse. The participating personnel members use multiple tools, such as scalpels, forceps, and others, varying according to the surgery being performed. Also used are multiple disposable items, such as sponges of various sizes, used for absorbing blood and other liquids, or other purposes.

Intensive efforts are invested in keeping track of all tools and disposables, in order to make sure no tool or disposable unintentionally remains inside the patient's body. Therefore careful counting is performed before, during and after the operation, including counting the used disposables thrown into the trash bins.

The counting is a tedious job and requires intensive resources, including mental resources, personnel time and down-time of the operating room. Counting the tools and disposables towards the end of an operation also increases the time the patient's body is open and the associated risks.

In addition, counting is not always error-free, and in too many cases tools or disposables end up being left within the patient's body, causing severe damage and even death.

Another problem relates to the life cycle of tools. For example, the tools used in an operation have to be sanitized or sterilized prior to further usage. Other constraints may relate to maintenance operations required for the tools, for example, a blade may have to be sharpened after every predetermined number of operations in which it is used. In another example, tools that have been used in an operation performed on a patient with a contiguous disease may require extra sterilization before further usage, or the like. Making sure that each tool is used and maintained properly also imposes expenses and requires resources, including record keeping and tracking, manual labor and the like. Currently there is no computerized formal procedure of tracking the tools, in order for example to avoid cases in which damaged instruments are brought back to the operating room. There is also no formal procedure in which the operating room personnel communicates with the Central Sterilizing Supply Unit (CSSU) personnel, as to the problems or condition of instruments and/or tools, which may be have disastrous consequences to patients.

Similar considerations exist in additional environments, such as hangars, garages or the like, in which it is necessary to make sure no tool or disposable is left within an engine, for example, before indicating it can be declared as functioning properly, and wherein tools may require periodical maintenance.

Current techniques do not provide answers to the technological difficulties associated with identification of tools, including insufficient coverage, identification when no contact is formed between a tool to be identified and an identifying device, problems caused by metallic environment or an intensive-radiation environment, such as an operation room, or others.

There is thus a need in the art for a system for tracking and identifying equipment including tools and disposables in a complex, optionally metallic, environment, in order to keep track of the equipment before, during and after using them, and in order to maintain the equipment according to the required standards.

SUMMARY

A method and apparatus for identifying and tracking instruments, in multiple instrument environments such as an operating room or a garage. Each instrument or disposable has attached thereto an identifying tag, such as an RFID tag. Each plane or location the instruments or disposables are placed on, comprises an antenna and thus continuously identifies the tools. In order for the antenna to work in a metallic environment, the antenna is equipped with a metallic board underneath, which insulates form other metals, and in order for the metallic board not to absorb all the energy, a spacing layer is placed between the metal board and the antenna. Flat antennas may be implemented as a collection of wire loops, overlapping in about 20% of one of their dimensions.

One aspect of the disclosure relates to an identification antenna for receiving signals from a tag attached to a tool or a disposable placed on the antenna, the antenna comprising: two or more loops made of conductive material, each loop partially overlapping with one or more other loops; a substantially flat conductive board; and a spacing layer, for keeping distance between the loops and the conductive board. The antenna optionally emits a signal having radio frequency, and the tag is optionally a Radio Frequency Identification (RFID) tag. Within the antenna, partially overlapping loops optionally substantially fully overlap in one dimension, and overlap in about 20 percents in the other dimension. The antenna can further comprise an insulating top cover or base cover. Within the antenna, the flat conductive board and the spacing layer optionally have width and depth substantially equal to the width and depth of an operation room instrument table, or of a table top of a Mayo. Within the antenna, the loops are optionally attached to an FR4 board. Within the antenna, the spacing layer optionally comprises crisscross spacing elements. Within the antenna, the conductive board optionally comprises an FR4 board covered with a conductive layer on its upper and lower planes. Within the antenna, each of the loops optionally comprises a capacitor. Within the antenna, information regarding the tag is optionally transferred by the antenna to a reader, and wherein information from the reader is transferred to a computing platform. Within the antenna, the computing platform optionally executes one or more applications selected from the group consisting of: generating a collection of available tools at the beginning of an operation; adding tools to the collection; removing tools from the collection, such as tools taken out of the room; receiving a report on all tools from the collection not identified in the preceding predetermined period of time; letting a user approve a missing tool; enabling operating room personnel and Central Sterilizing Supply Unit personnel to communicate regarding condition of instruments; and generating and providing a report about tools used during surgery that have to undergo special maintenance.

Another aspect of the disclosure relates to an identification antenna for receiving signals from a tag attached to a tool or a disposable placed within the antenna, the antenna comprising: an internal bucket, having attached to its external surface one or more loops made of conductive material; a conductive layer; a spacer for forming a distance between the loops and the conductive layer; and an external bucket for insulating the conductive layer.

Yet another aspect of the disclosure relates to an identification antenna for receiving signals from an RFID tag attached to a tool or a disposable placed within the antenna, the antenna comprising: an insulating bin, having attached to its external surface one or more loops made of conductive material; an insulating cover for covering the loops; a first spacing layer placed under the insulating bin; a conductive layer placed under the first spacing layer; and a second spacing layer placed under the conductive layer.

Yet another aspect of the disclosure relates to an tool to be identified by an identifying antenna, the tool comprising: one or more operative parts; a tag-holding part, comprising: a tag; a housing for the tag, shaped like a first ring and a second ring attached on their flat parts, wherein the first ring has an external diameter equal to the external diameter of the second ring, the first ring has an internal diameter larger than the internal diameter of the second ring, the internal diameter of the second ring compatible with the diameter of the tag, and the first ring having a notch; and an insulating cover for covering the tag and the first ring, excluding at least an area in which the first ring is connected to an operative part.

BRIEF DESCRIPTION OF THE DRAWINGS

The present invention will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

The following disclosure relates to an environment in which multiple tools or disposables have to be identified or racked. Although the detailed exemplary embodiments relate to an operation room environment, the constraints as well as the presented implementation details are similar to other environments, such as garages, hangars or others.

The disclosure relates to equipping all tools and disposables with a Radio Frequency Identifier (RFID) tag, and equipping all possible locations for the tools and disposables with antennas for identifying the tools and disposables. The identified items are continuously monitored by a computerized application.

Existing RFID systems suffer from a number of problems which makes them inadequate to an operation room environment. First, the operation room is a highly-metallic environment, since many of the tools, furniture and other items in the room are made of metal. The metallic environment shifts the resonance frequency of the tag and can thus eliminate proper identification. Another problem stems from the multiplicity of electro-magnetic radiation sources in the room, including monitors, sensors, pace makers, and other equipment.

Yet another problem refers to the contact required between the tag and the antenna. An operation room is a complex environment, and additional requirements, such as placing the tools in a certain direction or position can not be enforced. Thus, contact between the tool and an antenna can not be guaranteed, which also harms identification.

Figure 1:
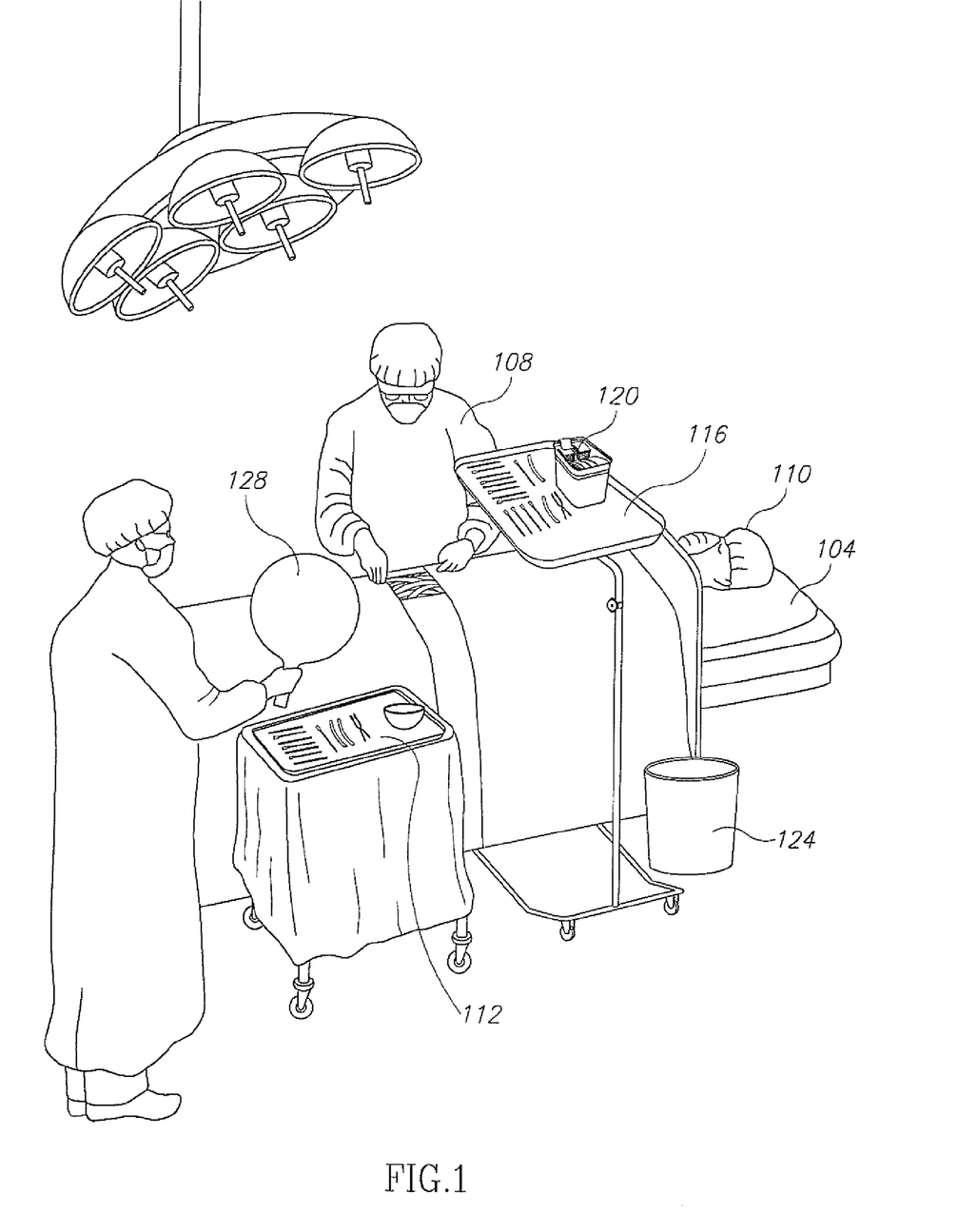
FIG. 1 is a schematic illustration of an operation room, comprising multiple objects on which tools or disposables can be placed, in accordance with the disclosure.

These problems are solved by incorporating antennas into all locations in which the tools and disposables are placed, wherein the antennas are not influenced by the metallic environment, and are sensitive enough to identify tags up to a few centimeters apart from the antenna, and in various angles. FIG. 1 shows a schematic illustration of an operation room, with said locations functioning as antennas. The various locations and the details of the antennas are provided in association with FIGS. 3, 4, 5 and 6 below. FIGS. 7A, 7B and 7C provide the details for attaching a tag to a tool.

Referring now to FIG. 1, there is shown a schematic illustration of an operation room, in which an identification and tracking system and method are required.

A typical operation room comprises an operation bed 104 on which a patient 110 being operated on lies. A surgeon 108 stands by patient 110 and operates on him. Surgeon 108 receives the tools as required from a scrub nurse who takes the tools from an instrument table 112. The tools may be placed on instrument table 112 by a circulating nurse who does not touch the tools but only opens their wraps.

Surgeon 108 or another team member can place tools on a moveable tray 116 placed above or near patient 110, often called a Mayo.

Each operation room typically has one or more instrument tables and one or more Mayos, depending on factors such as the complexity of the surgery, number of surgeons and other team members, personal preferences or others.

The team members retrieve clean sponges from one or more clean sponge bins or dispenser 120, and throw the used ones into one or more waste buckets 124.

Thus, at the end of the surgery, all tools and disposables that were in the operation room prior to the surgery, should be on instrument table 112, on Mayo 116, in clean sponge bin 120 or in waste bucket 124 (collectively referred to as the "utilities").

Prior to the beginning of the surgery, all tools and disposables available to the team are registered. In order to eliminate all manual counting, an RFID tag is attached to any tool and disposable item. The registration can include identification, for example for a non-disposable tool, or only indicating the number of items of each type, for example the number of sponges of a particular type. All utilities on or in which the tools and disposables are placed are equipped with antennas, such that the tools and disposables placed on or in the utilities are continuously tracked and possibly identified. Then, at the end of the surgery, or at any other time, the registered tools and disposables are compared against the tracked tools and disposables, and missing items are identified.

The operation room is also equipped with a wand 128, which is also an antenna, and which is used for identifying and tracking items within the body of patient 110, by waving the wand near patient 110. Wand 128 can also be used for introducing to the system additional tools or disposables after the initial registration, for example if an extra pack of sponges or extra tools are required.

Figure 2:
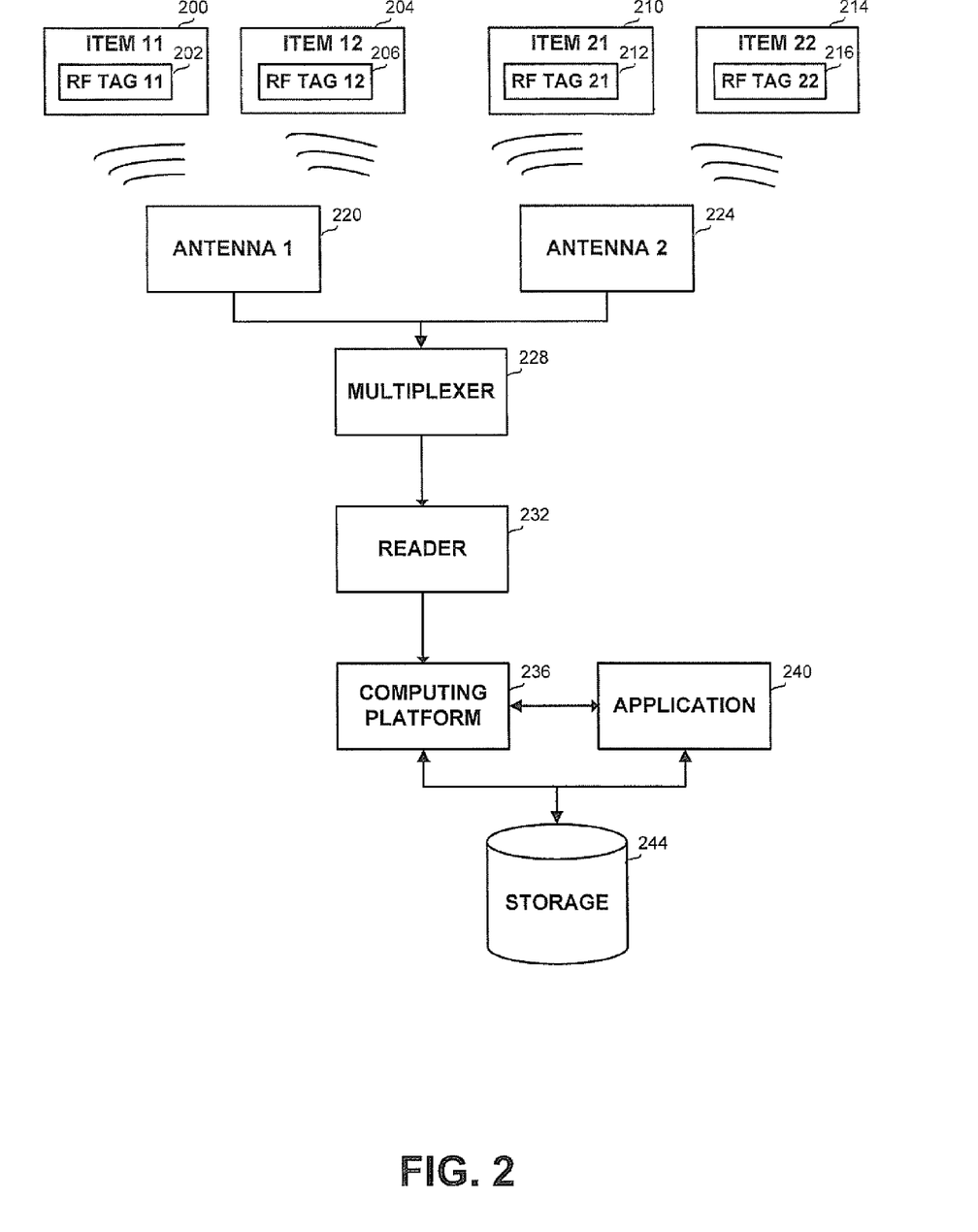
FIG. 2 is a schematic illustration of a Radio Frequency Identification system, in accordance with the disclosure.

Referring now to FIG. 2, there is shown an RFID identification system, as used for identifying the multiple items. An RFID system is intended for identifying one or more items. To each item to be identified, such as item 11 (200), item 12 (204), item 21 (210) or item 22 (214), a tag is attached which is carries a unique identifier. The tag is optionally an RFID tag. In FIG. 2, item 11 (200) carries tag 11 (202), item 12 (204) carries tag 12 (206), item 21 (210) carries tag 21 (212), and item 22 (214) carries tag 22 (216). Each tag can be readable and optionally writeable. In the context of the disclosure, write-once tags are used, which are manufactured to carry the unique identifier, for example by burning the identifier onto the tag.

Each tag receives signals from one or more antennas, such as antenna 1 (220) or antenna 2 (224), and emits a signal carrying its unique identifier. The antennas are used for drawing energy from the signal to energize the tags and for communicating between the tags and the reader. The geometric shape of the antenna is central to the operation of the system. In the context of the disclosure, the antennas are located on the instrument table, on the top part of the Mayo, in the trash bin, in the clean sponge bin, and in the wand.

Tags can be active or passive, wherein active tags contain their own power source. Passive tags use the power emitted from the reader via the antenna as an energy source. In the context of the disclosure, due to the sizes of the items, their quantity, and that some of the items are disposable, passive tags are preferable.

The signal emitted by each antenna can be received by multiple tags, and the signal emitted by each tag can be received by multiple antennas.

The signals received by all antennas are transferred to multiplexer 228 which multiplexes the signals, and transfers them to reader 232. Reader 232 identifies the unique identifiers whose signals were received, and transfers the data via any interface, such as RS232 to computing platform 236. In the context of the disclosure, multiple readers may be used, such as but not limited to HF-LR, HF-LRMG1, or EzMUX-HF by Kenetics of Jersey, Great Britain (www.keneticsgroup.com). The multiplexer can be selected, among other factors, on the number of antennas it can support simultaneously.

Computing platform 236 can be a personal computer, a mainframe computer, or any other type of computing platform provisioned with a memory device (not shown), a CPU or microprocessor device, and several I/O ports (not shown). Computing platform 236 executes one or more applications 240, which are interrelated sets of computer instructions programmed in any programming language and under any development environment. Any of applications 240 can store and retrieve data from storage device 244, which is a mass storage device, for example an optical storage device such as a CD, a DVD, or a laser disk; a magnetic storage device such as a tape or a hard disk; a semiconductor storage device such as Flash device, memory stick, or the like. Any of applications 240 can, for example, maintain a list of all tags available at the operation room prior to the surgery, and produce periodically a report for all items not reported since the last report.

Computing platform 236 together with one or more applications 240 can be implemented as firmware ported for a specific processor such as digital signal processor (DSP) or microcontrollers, or can be implemented as hardware or configurable hardware such as field programmable gate array (FPGA) or application specific integrated circuit (ASIC).

Multiple applications can be used in order to track, identify and maintain tag carrying tools and disposables. Multiple applications may access the same or different databases or otherwise stored relevant information, such as when was the last time the tag was identified, which antenna was the tag identified by, or the like.

Thus, the applications can provide any one or more of the following options: generating a collection of available tools at the beginning of an operation; adding tools to the collection; removing tools from the collection, such as tools taken out of the room; receiving a report on all tools from the collection not identified in the preceding predetermined period of time; letting a user indicate a missing tool as "OK"; enabling operating room personnel and Central Sterilizing Supply Unit personnel to communicate regarding the condition, problems and maintenance of instruments; generating and providing a report after about all tools used during surgery that have to undergo special maintenance; or the like.

It will be appreciated that multiple other applications and options can be designed to support the specific operations, procedures, and requirements in the particular environment.

In the context of operation rooms, the signal emitted by the tags has to be of a predetermined frequency, which is approved for such environment. In some environments, this frequency is 13.56 MHz. This frequency provides good performance in liquid medium, in metallic environment and is relatively resistant to electromagnetic noise.

Figure 3:
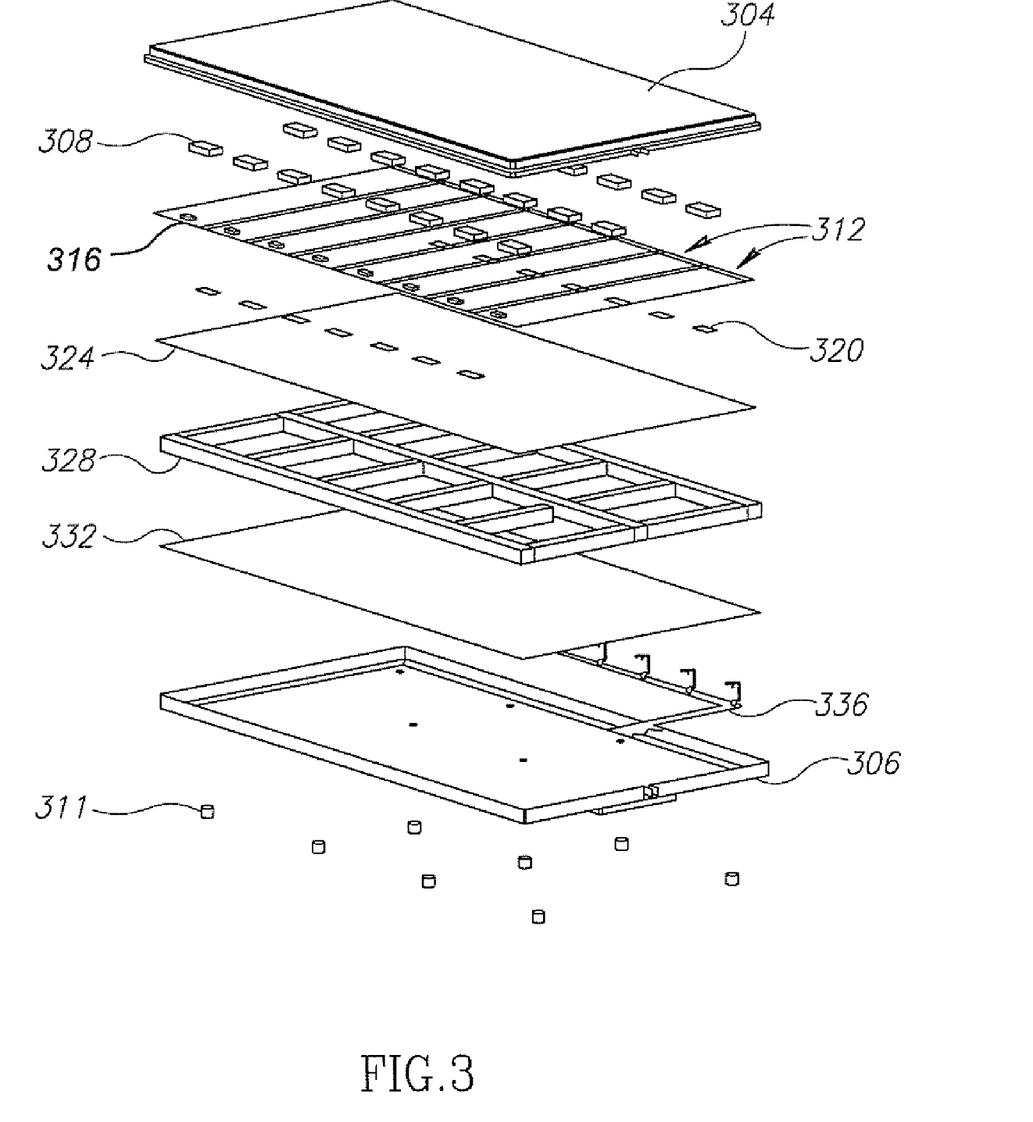
FIG. 3 is a schematic illustration of a flat antenna for identifying tools or disposables, in accordance with the disclosure.

Referring now to FIG. 3, there is shown an exploded view of a flat antenna. The flat antenna is placed on the table top of the instrument table, or on the table top of the Mayo, such that the tools and disposables are placed on the flat antenna. The flat antenna is required to identify the RFID tag-carrying tools placed thereon.

The flat antenna is generally made of a non-conductive case, containing multiple partially overlapping flat wire loops forming the physical antennas. It is required to eliminate influences of the metallic environment, such as the operation room, on the flat antenna and form a stable known metallic environment for the antennas so that the antenna emits signals of stable frequency. Therefore, the flat antenna comprises a metallic layer placed under the wire loops, i.e. between the wire loops and the underlying plane on which the antenna is placed. Thus, other metallic objects, such as the table tops of the instrument table or the Mayo, do not create unexpected effects and do not affect the frequency of the antenna. However, the metallic plane can absorb at least part of the energy emitted by the antennas and reduce the coverage. Therefore, space is formed between the wire loops and the metallic layer.

One implementation of a flat antenna, as depicted in FIG. 3 comprises the components as detailed below, arranged in layers.

The flat antenna can vary in size according to the dimensions of the plane on which it is to be placed, such as the instrument table. Typically, the width and length of the antenna vary between about 10 cm and 150 cm.

The flat antenna comprises a top cover 304 and a base cover 306 enclosing the antenna from its top and bottom. Top cover 304 and base cover 306 are made of non-conductive material such as plastic, wood, plywood or the like. The bottom surface of base cover 306 may be provided with anti sliding elements 311.

Under top cover 304 there are multiple spacers 308, intended to keep top cover 304 at a constant distance from antenna loops 312. The distance is required in order to keep loops 312 from redundant pressure, and to allow cooling of the loops. Spacers 308 are also made of non-conductive material, and can vary in size and density. Each spacer is preferably a rectangular prism. In the embodiment shown in FIG. 3, there are 24 spacers, the height of which is between about 0.5 cm and 3 cm, and the width and length are between a few millimeters and a few centimeters.

Underneath spacers 308 are multiple antenna loops 312. Each of antenna loops 312 is a loop of conductive material, such as a copper strip, having a width between about 1 mm and about 20 mm, and thickness of between about 0.1 mm and 1 cm. However, a problem that occurs when multiple antennas are placed in proximity to or overlap one another relates to the loss of calibration due to the mutual influence of the metal of each antenna on the resonance frequency of the other. This problem is solved by a particular overlapping arrangement of the loops, such that the loops fully overlap in one dimension, and overlap by about 20% in the other dimension, for loops ranging in width between about 3 cm and about 30 cm. Thus, if any two neighboring loops overlap by about 20%, their frequencies do not influence each other. The loops may vary in width from about 1 cm to about 30 cm. The loops' depth is substantially equal to the flat antenna depth. In each loop is a capacitor 316 responsible for generating the required resonance frequency of the antenna, such as the frequency of 13.56 MHz. In some embodiments, instead of a single capacitor 316, a constant capacitor and a variable capacitor can be used, to enable fine tuning of the frequency. For example, the constant capacitor can have capacity of between 50 pF and 500 pF, and the variable one of capacity between 3 pF and 20 pF.

The output of all capacitors 316 is transmitted to the multiplexer of the system.

The multiplexer activates the flat antenna plane in a time-share manner, i.e. at any given time at most one antenna loop emits a signal. The signal-emitting loop changes every predetermined period of time, such as between 10 milliseconds and 1000 milliseconds. Once a particular loop emits a signal, all other antennas emit signals before the particular loop emits the signal again. The signal-emitting loop preferably changes in a constant loop.

The time-share signal emitting enhances the coverage of the flat antenna and ensures that more tools are identified. This is because of the following: if the whole plane was surrounded by a single loop constantly providing a predetermined amount of energy, on average more metallic tools would have been surrounded by the loop than are surrounded by a smaller loop. Therefore, a significant part of the energy would have been absorbed by these tools, and some of the tools would have not been recognized. If the same amount of energy is emitted by a smaller loop encircling fewer tools, less energy is absorbed by the tools and more tools or disposables are identified. It is not required to continuously identify every tool. Therefore, if the pace at which the signal emitting loop changes is between about 0.125 and 1000 times a second, and a flat antenna comprises eight loops, every tool is identified at least every second, which is sufficient for all practical purposes. It will be appreciated that the pace at which the signal emitting loop changes, and the number of loops are derived from the practical requirements as to the minimal or maximal number of tools that should be identified, and how often should each tool be identified at the minimum.

The energy being emitted to a smaller part of the plane rather than the whole plane also ensures that tools whose tag is not in contact with the plane but is a few centimeters above it, or tools whose tag is not parallel to the plane but forms a non-zero angle with the plane are identified as well. The required energy level is derived from the size of the loops and the required coverage performance, i.e. what is the height and angle of tools that have to be identified.

Underneath antenna loops 312 are optional insulator patches 320, for attaching antenna loops 312 to an insulator layer such as an FR4 board 324, such as a board used for printed circuit boards (PCBs). Board 324 is substantially of the same width and length as the antenna.

Underneath board 324 is a spacing layer 328 made of spacers, designed to create space between antenna loops 312 and conductive board 332. In order to not unnecessarily increase the weight of the flat antenna, spacers 324 may not form a solid layer, but may be arranged so that antenna loops 312 are kept at a fixed distance from conductive board 332. Spacers 328 can be placed at any required arrangement such as a crisscross. Spacers 328 can be made of any insulating material, such as wood, Styrofoam, or the like.

Underneath spacers 328 is conductive board 332. Conductive board 332 can be generated from an FR4 board similar to board 324, which is wrapped or coated on its top and bottom planes by a conductive layer, such as a copper sheet 1/1 oz.

Underneath conductive board 332 is cable arrangement 336, which is connected to a power source (not shown) and supplies power to antenna loops 312.

The disclosed flat antenna structure enables flexibility in the construction of antennas of varying sizes. By increasing or reducing the number of antenna loops according to the required flat antenna size, and changing the loops' size, antennas of any size can be generated, without extensive tests and calibrations.

It will be appreciated that the disclosed flat antenna can be used also in non-horizontal positions. For example, the flat antenna can be used as a rear wall of an instrument cupboard, for identifying tools hung in the cupboard. The tools should be stored using non-conductive means, such as non-conductive nails, or non-conductive shelves.

Figure 4:
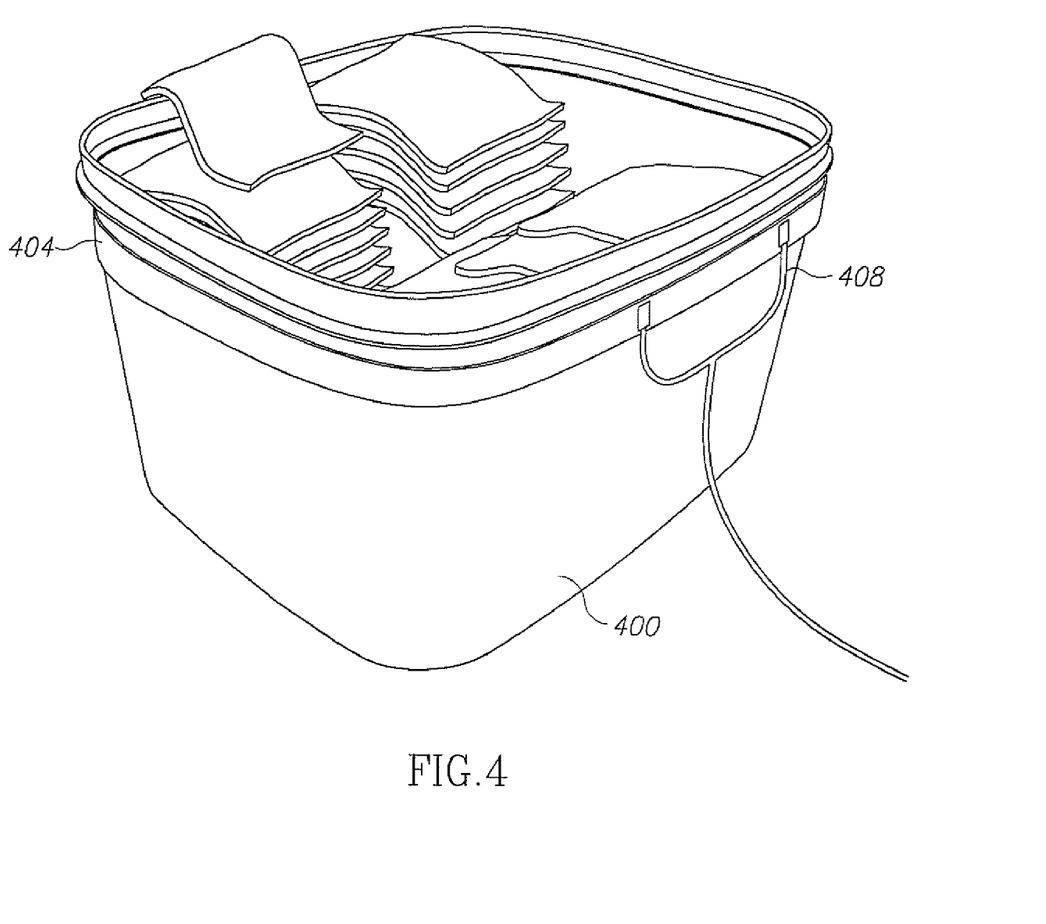
FIG. 4 is a schematic illustration of a clean sponge bin for identifying tools or disposables, in accordance with the disclosure.

Referring now to FIG. 4, there is shown a schematic illustration of a clean sponge bin for containing and identifying tools or disposables. As part of tracking and identifying all tagged items, the tagged items in the clean sponge bin have to be identified as well, thus the bin also serves as an antenna for identifying objects. The bin is usually a rectangular container 400 open at its upper end, although any other open container can be used as well. The bin is sized so as to comfortably contain clean sponges required for the surgery. Exemplary dimensions for a substantially rectangular-based bin can range between about 5 cm and about 40 cm for the width and the height of each wall of the bin, a diameter of between 5 cm and 20 cm for a round-based bin, or the like. The bin is made of non-conductive sterilizable material. The external side of the bin is encircled by a conductive loop 404. Loop 404 is optionally made of wire similar to the wire making up wire loops 312 of the flat antenna of FIG. 2. In some embodiments, the loop is made of a copper strip having a width of a few millimeters, such as 5 mm, and is between 0.1 mm and 5 mm thick. The wire preferably but not mandatory encircles the bin on a constant height, which can vary between about 0.5 cm above the bottom of the bin and about 0.5 cm under the top rim of the bin. Loop 404 receives power supply through cable structure 408 which connects the loop to a power source. The ends of loop 404 are connected to a capacitor (not shown) responsible for generating the required resonance frequency of the bin antenna. In an operation room environment this frequency is preferably 13.56 MHz. As with the flat antenna of FIG. 2, the capacitor can be implemented as two capacitors, a constant capacitor having capacity of between 50 pF and 500 pF, and a variable capacitor having capacity between 3 pF and 20 pF, for fine-tuning.

It will be appreciated that loop 404 is optionally covered by an insulating cover (not shown). The insulating cover can have a hole in a location corresponding to the capacitor in order to fine tune the capacity.

Since the bin can be placed anywhere in the operation room, including on a metallic plane which can disturb the resonance frequency of the antenna. Therefore, in order to create a known stable metallic environment, so that the resonance frequency of the bin antenna will not be influenced by the arbitrary plane underneath, a metallic layer is may be placed under the bottom of the bin. However, since the metallic layer may absorb part of the energy emitted by the antenna, a spacer layer is placed between the bottom of the bin and the metallic layer. Yet another spacer layer may be placed underneath the metallic layer, to prevent possible disturbance of the metallic layer to other antennas, for example in the case that the bin is placed on the flat antenna described in association with FIG. 3 above.

Thus, a three-layer basis may be attached to the bottom of the bin, comprising a spacer, a metallic layer and another spacer. Each of the spacer layers can be made of plastic, Styrofoam, wood or another non-conductive material and should have a minimal height of about 5 mm. The metallic layer can be made of a copper-coated PCB board or any other conductive layer.

Figure 5:
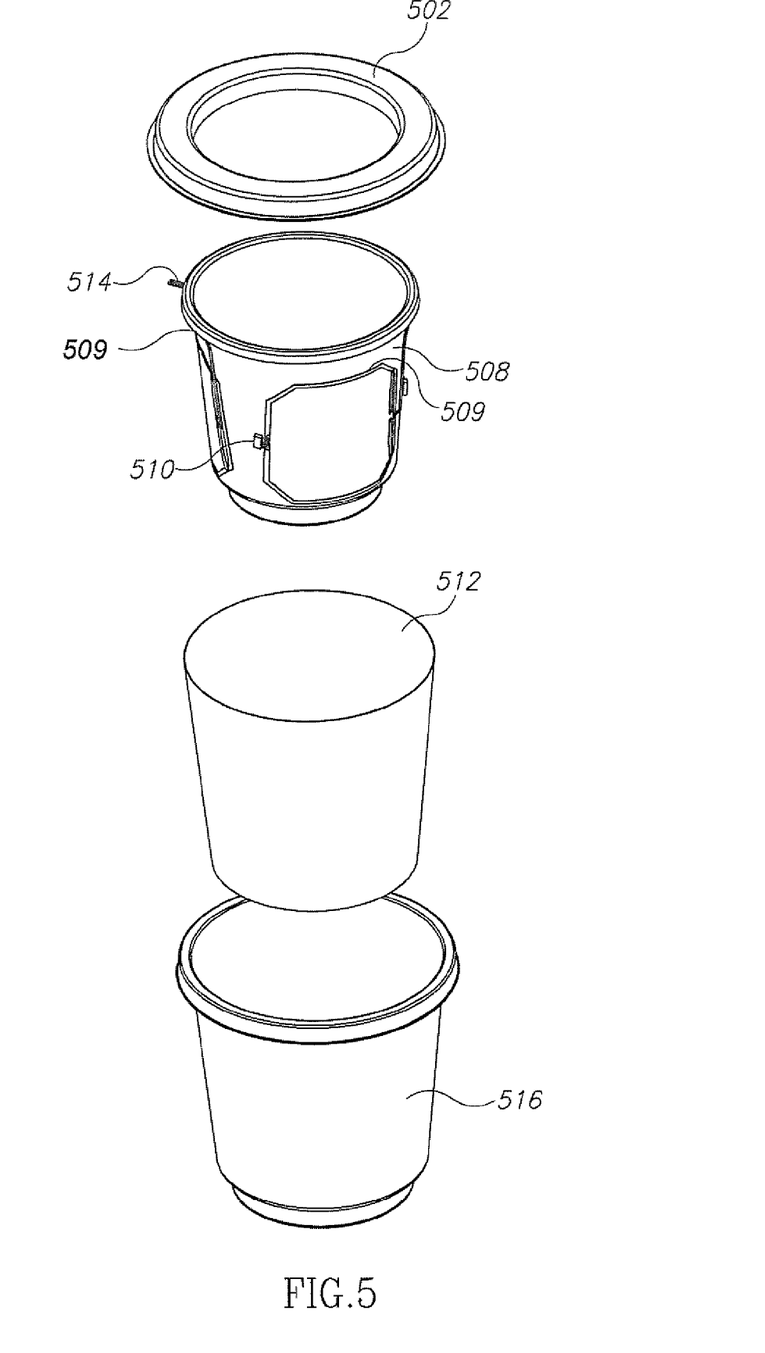
FIG. 5 is a schematic illustration of a trash bin for identifying tools or disposables, in accordance with the disclosure.

Referring now to FIG. 5, there is shown a schematic illustration of a trash bin which also serves as an antenna, and identifies items such as used tagged sponges or other tagged articles within the bin.

Similarly to the mechanism detailed in association with FIG. 3 and FIG. 4 above, the trash bin comprises a bucket with a conductive loop and electrical components so that it forms an RFID antenna. In order to eliminate influences of the metallic environment on the antenna, there is a metallic layer around the bucket which provides a known stable metallic environment, and in order to prevent the metallic layer from absorbing the energy emitted by the loop, a space is formed between the metallic layer and the bucket.

This is achieved, as can be seen in FIG. 5 by using two buckets, placed one within the other. The inner bucket is smaller than the external bucket and comprises multiple wire loops, and the external bucket is covered on its inside by a metallic layer. The two buckets are kept at a constant distance from one another by plastic or other spacers placed between the buckets, which eliminate the inner bucket from moving within the external bucket.

The bucket structure thus comprises a top cover 502, made of insulating material, such as plastic. The structure further comprises an internal bucket 508 also made of insulating material, which has attached to its external surface one or more antenna loops, for example three loops such as loop 509. The loops are preferably substantially equally distributed around the internal bucket. Each loop is made of conductive material, such as loop 404 around the clean sponge bin of FIG. 4. The loop can be round, rectangular, trimmed-corner rectangle or of any other shape. The term "round" or "rectangular" in this context refer to the shape as spread flat. Naturally when placed over a substantially cylindrical object such as the internal bucket, the shape changes accordingly. The loop can be made of, for example, from a copper strip having a width between about 1 mm and about 20 mm, and thickness of between about 0.1 mm and 1 cm. Loop 509 contains capacitor 510, similar to any of capacitors 316 of FIG. 3 above. The capacitor is connected via a wire (not shown) to the multiplexer of the system. The loops are connected therebetween and receive power supply from a power source through cable 514.

The structure further comprises conductive layer 512 and external bucket 516 made of insulating material. Conductive layer 512 can be implemented as a metallic net, or as an adhesive layer, such as a copper strip 1/1 oz, which is attached to external bucket 516 on its internal side.

It is required to keep a fixed distance between antenna loops 509 and conductive layer 512, so that conductive layer 512 does not absorb significant energy emitted by loop 509, and thus reduce coverage. For forming the distance, internal bucket 508 may comprise at least two spacers on its external side (not shown), which may be structured like a cube or in any other shape. The thickness of the spacer should be half the difference between the diameter of the internal and the external buckets, so that when the internal bucket with the spacers is placed within the external bucket, there is no relative movement between the two buckets.

In order to fine-tune the frequency of loop 509, access openings may be drilled in external bucket 516 in order to enable access to capacitors 510.

It will be appreciated by persons skilled in the art that the loops can be arranged on the internal bucket in a multiplicity of ways. For example, a possible arrangement comprises a loop encircling the bucket at about half the height of the buckets, and two or more loops similar to loop 509 but of smaller size at the upper and at the lower parts of the bucket.

Figure 6:
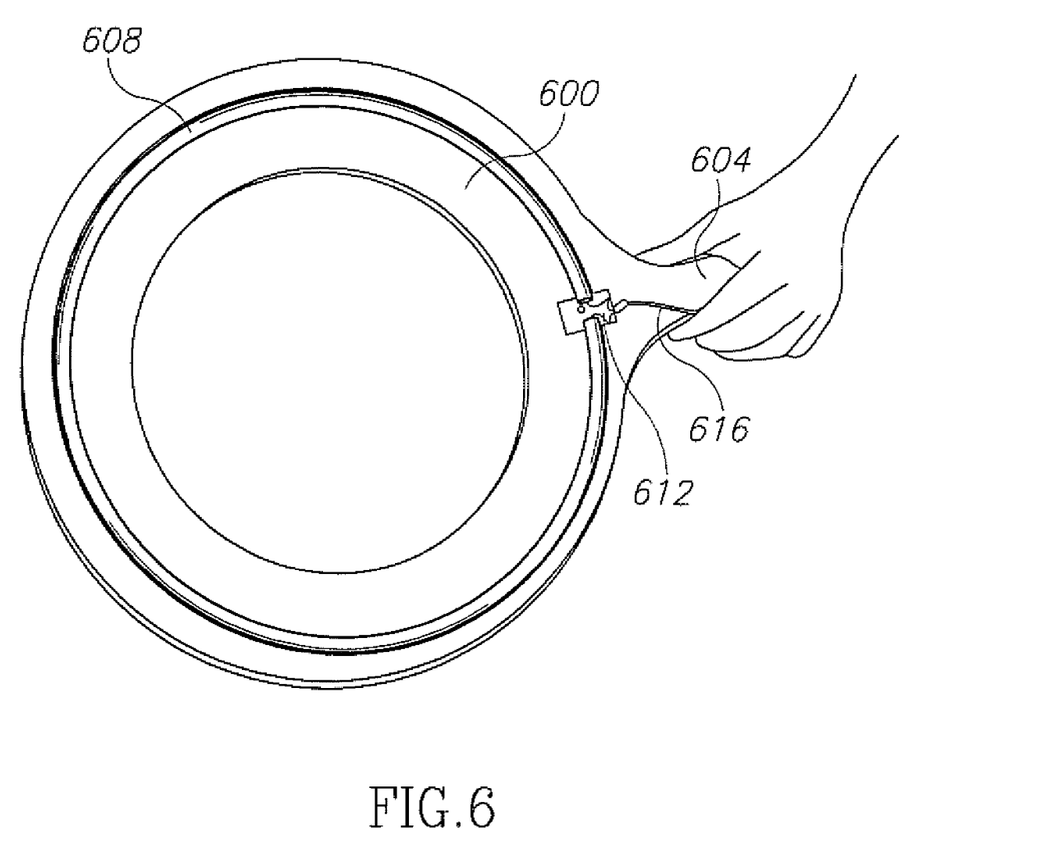
FIG. 6 is a schematic illustration of an identifying wand, in accordance with the disclosure.
Figure 7A:
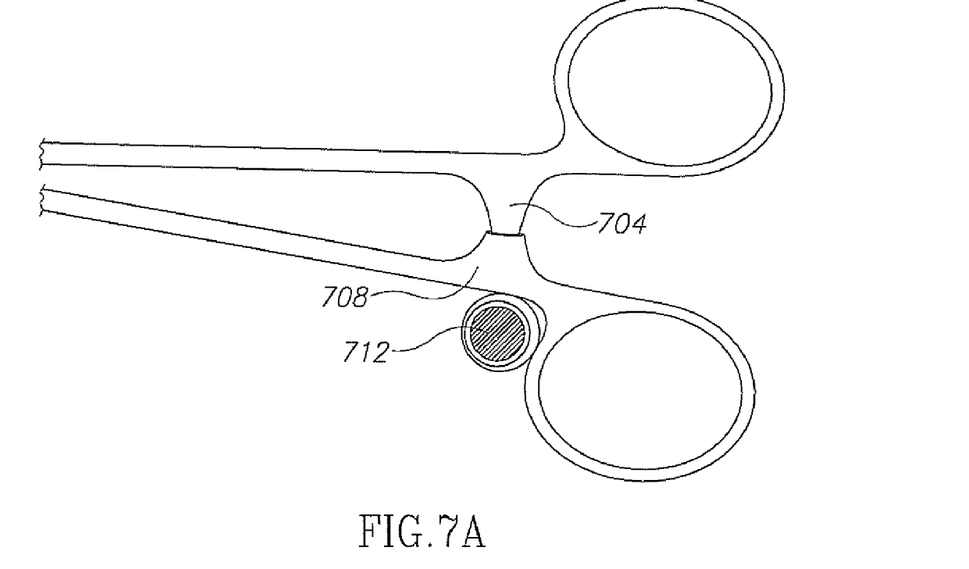
FIG. 7A is a schematic illustration of a tool having an identification tag attached thereto, in accordance with the disclosure.
Figure 7B:
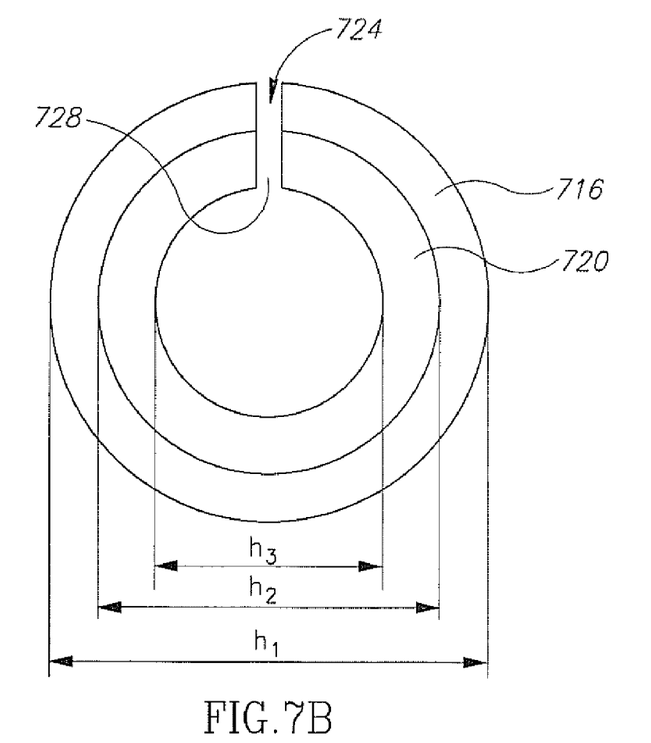
FIG. 7B is a top view of a tag-holding part for attaching a tag to a tool, in accordance with the disclosure.
Figure 7C:
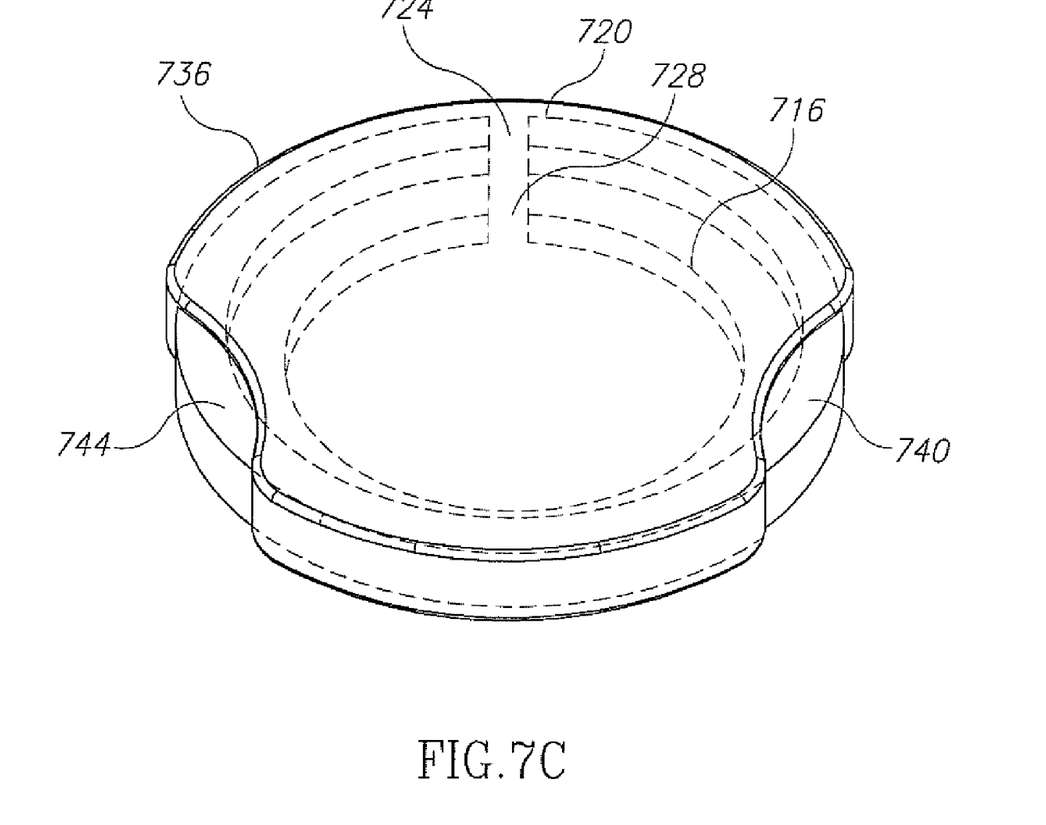
FIG. 7C is a perspective view of the tag-holding part of FIG. 7B with a cover, in accordance with the disclosure.

Referring now to FIG. 6, there is shown a top view of a wand for identifying items carrying RFID tags. The wand also serves as an antenna in an RFID identification system, such as the system detailed in association with FIG. 2 above. The wand is a ring-like instrument, made of non-conductive material, such as FR4. The wand has a main area 600 preferably substantially round and a handle 604. Alternatively, main area 600 can be of any other shape, such as rectangular. The wand has near its perimeter, for example at a distance between about 0.1 mm and about 2 cm from its perimeter a wire loop 608, made of wire similar to the wire of any of the loops of the antenna of FIG. 3. At one point of loop 608 there is a capacitor 612 designed for generating the required resonance frequency of the wand antenna frequency as required. In an operation room environment this frequency is preferably 13.56 MHz. Capacitor 612 is connected at its other end to a multiplexer which is connected to an RFID reader. In order to enable fine tuning of the wand's frequency, capacitor 612 may also be implemented as two capacitors, a constant capacitor having capacity of between 50 pF and 500 pF, and a variable capacitor having capacity between 3 pF and 20 pF. At or near the part of loop which connects to capacitor 612, the loop is also connected to a wire connected on its other end to a power source, for providing power to the loop.

The wand can be used in a multiplicity of ways. One exemplary usage is for locating missing tagged items that were not detected by any of the other antennas. When searching for items, the wand is brought near an area in which the items may be, such as near the patient's body. In another exemplary embedment, the wand is used for introducing to the operation room additional items beyond the items usually introduced when preparing the operation room. Such items may include items out of pre-prepared sets, such as special or additional tools, or items added during the surgery, such as extra sponges.

Referring now to FIG. 7A, shown is an exemplary surgery tool having attached thereto an RFID tag. The tool comprises its normal operative components 704, 708, and an additional inseparable tag-holding part 712 which is designed to hold an RFID tag.

The tags used for identifying tools and disposables should be lightweight and durable. In order to meet the existing standards for tools, the tags should be resistant to at least 2000 cycles of sterilization, which means temperature of at least 134 degree centigrade for at least 18 minutes. In some embodiments, tags as 10 mm tags manufactured by Vonskee of Tradehub, Singapore (www.vonskee.com), or 16 mm tags manufactured by Tagsys RFID Group, Inc. of Burlington, Mass., USA can be used.

The tags should be attached to the tool in such manner that does not interfere with the operation of the tool. Yet another requirement is that the position at which the tool is normally set (for example, scissors are usually placed horizontally and not vertically), the tag will not be vertical.

Referring now to FIG. 7B, there is shown the tag housing part of part 712, which is attached to the tool and preferably made of the same material as the tool, so no additional sterilization problems arise. The tag housing is substantially round, and is shaped like two rings, a first ring 716 and a second 720, attached on their flat part. Ring 716 and ring 720 have the same external diameter h1. Ring 716 has an internal diameter h2 which is larger than the internal diameter of ring 720, h3. The internal diameter of ring 716, h2, is arranged so that the used RFID tag can be inserted into the ring 716 and rest on ring 720 without moving.

Ring 716 and ring 720 have notches 724 and 728, respectively, at corresponding locations, so that the signal emitted by the tag will not be completely absorbed by the rings. In some embodiments, a notch on ring 716 may be enough, so notch 728 can be omitted. It will be appreciated that in some embodiments the tag housing part can be manufactured as a single part, and the two ring structure is used for explanatory purposes only.

Referring now to FIG. 7C, there is shown the ring structure of FIG. 7B, as covered by an insulating sturdy bio-compatible cover 736 so as to eliminate contact between the tag and the patient's body. Cover 736 should also be resistant to at least 2000 cycles of sterilization. Cover 736 should expose the rings in at least one area such as exemplary areas 740, 744 in order to weld or otherwise attach the ring structure to the tool.

It will be appreciated that tags connected to disposable items, such as sponges should be able to resist the same procedures which the items undergo, such as sterilization. It will also be appreciated that the tags should have a bio compatible exterior, and should be attached to the items in a manner that will ensure that the tags will not be incidentally removed. Tags as used in commercial laundries, such as tags manufactured by Daily RFID Co. of China (http://www.rfid-in-china.com) can be used for such purposes.

The disclosed system comprises multiple antennas in order to identify and track multiple tag-carrying items. The antennas are integrated into the locations at which the tagged items may be present, such as the instrument table, Mayo, trash bin, and clean sponge box. All disclosed antennas. In order to perform in a stable manner in a highly metallic environment are equipped with their own metallic layers, which provide a known stable metallic environment which is taken into account while tuning the antenna. Then, in order for the metallic layer not to absorb large parts of the energy emitted by the antenna, a known and constant space is maintained between the antenna and the metallic layer.

It will be appreciated by a person skilled in the art that the disclosure teaches the design of additional antennas according to the disclosed principles, comprising a constant known metallic environment, which is at a constant known distance from the antenna. It will also be appreciated that the disclosure is not limited to a particular environment, and that antennas constructed according to these principles can be used in any environment, including garages, hangars, warehouses, artist studios, production lines, or the like.

The disclosure is also relevant for other identification protocols which can operate without contact between the tag and the antenna, and is not therefore limited to RFID. The antennas and tools can communicate using any known protocol, and the results may be processed by any application.

It will be appreciated by persons skilled in the art that the present disclosure is not limited to what has been particularly shown and described hereinabove. Rather the scope of the present disclosure is defined only by the claims which follow.

What is claimed is:

1. A flat identification antenna for receiving signals from multiple tags, attached to tools or disposables placed on the antenna, the antenna comprising:
    at least two planar loops made of conductive material, each loop partially overlapping with at least one other loop of the at least two loops;
    a substantially flat conductive board positioned at a constant distance from said at least two planar loops in parallel thereto; and
    a spacing layer, for keeping the constant distance between the at least two planar loops and the conductive board.

2. The antenna of claim 1 wherein the antenna emits a signal having a radio frequency, and the tag is a Radio Frequency Identification (RFID) tag.

3. The antenna of claim 1 wherein the at least two planar loops are of a substantially rectangular shape having a first dimension and a second dimension, and wherein the at least two planar loops substantially fully overlap in the first dimension, and overlap by about 20 percents in the second dimension.

4. The antenna of claim 1 further comprising an insulating top cover or base cover.

5. The antenna of claim 1 wherein the flat conductive board and the spacing layer have width and length substantially equal to the width and length of an operation room instrument table, or of a table top of a Mayo.

6. The antenna of claim 1 wherein the at least two loops are attached to an FR4 board.

7. The antenna of claim 1 wherein the spacing layer comprises crisscross spacing elements.

8. The antenna of claim 1 wherein the conductive board comprises an FR4 board covered with a conductive layer on its upper and lower planes.

9. The antenna of claim 1 wherein each of the at least two loops comprises a capacitor.

10. The antenna of claim 1 wherein information regarding the tag is transferred by the antenna to a reader, and wherein information from the reader is transferred to a computing platform.

11. The antenna of claim 10 wherein the computing platform executes at least one application selected from the group consisting of: registering a collection of said tools which are available at a beginning of an operation, each of the tools in the collection having a tag identifiable by said antenna; adding tools to the collection; removing tools from the collection; providing a first report on all tools from the collection not identified in a preceding predetermined period of time; and providing a second report about tools used during said operation that have to undergo special maintenance.

12. The antenna of claim 11 wherein said collection of tools includes medical instruments and/or disposables available at a beginning of a surgery operation.

13. The antenna of claim 12 wherein said computing platform is further configured to enable operating room personnel and Central Sterilizing Supply Unit personnel to communicate regarding a condition of said instruments.

14. An identification bin configured for receiving signals from multiple tags attached to tools or disposables placed within the bin, the bin comprising:
   an internal bucket made of insulating material, having attached to its external surface two or more loops made of conductive material;
   an external bucket made of insulating material;
   a conductive layer attached to the internal surface of the external bucket; and
   a spacer for forming a constant distance between said internal and external buckets.

15. A tool to be identified by an identifying antenna, the tool comprising:
   at least one operative part;
   a tag-holding part, comprising:
      a tag;
      a housing for the tag comprising a first flat ring and a second flat ring attached to a flat side of the first flat ring, wherein the first ring has an external diameter equal to the external diameter of the second ring, the first ring has an internal diameter larger than the internal diameter of the second ring, the internal diameter of the second ring is compatible with the diameter of the tag, and the first and the second rings having a notch; and
   an insulating cover for covering the tag and the first ring, excluding at least one area in which the first ring is connected to the at least one operative part.

* * * * *